United States Patent [19]

Kensey et al.

[11] Patent Number: 4,747,821
[45] Date of Patent: May 31, 1988

[54] CATHETER WITH HIGH SPEED MOVING WORKING HEAD

[75] Inventors: Kenneth Kensey, Hinsdale, Ill.; John Nash, Downingtown, Pa.

[73] Assignee: Intravascular Surgical Instruments, Inc., Frazer, Pa.

[21] Appl. No.: 921,973

[22] Filed: Oct. 22, 1986

[51] Int. Cl.⁴ .............................................. A61B 17/00
[52] U.S. Cl. .................................. 604/22; 128/303 R; 128/305
[58] Field of Search ...................... 128/305, 305.1, 304, 128/303 R, 751–755; 604/22

[56] References Cited

U.S. PATENT DOCUMENTS

| 3,730,185 | 5/1973 | Cook et al. | 128/303 R |
| 4,445,509 | 5/1984 | Auth | 128/305 |
| 4,631,052 | 12/1986 | Kensey | 128/304 X |

FOREIGN PATENT DOCUMENTS 3421390  12/1985  Fed. Rep. of Germany ...... 128/328

*Primary Examiner*—Michael H. Thaler
*Attorney, Agent, or Firm*—Caesar, Rivise, Bernstein, Cohen & Polotilow, Ltd.

[57] ABSTRACT

A flexible, small diameter catheter for effecting various surgical procedures, such as opening a restriction formed of an undesirable material, e.g., atherosclerotic plaque, in a lumen, e.g., an artery, of a living being. The catheter includes a working head having at least one, non-sharp impacting surface arranged to be moved, e.g., rotated, at a high rate of speed by an associated drive means within the catheter. The catheter with the moving working head is brought into engagement to effect the opening of the restriction by dilating the artery and/or removing undesirable material therefrom. The removal of undesirable material results from the impacting surface impacting the material of the restriction repeatedly. A fluid is provided through the catheter to the working head and a portion is thrown radially outward. The fluid at the working head also flows in a vortex to cause any particles broken off from the restriction back to the moving working head where they are impacted again and again to further reduce their size. Such action creates particles of sufficiently small size that they may be enabled to flow distally without significant deleterious effects to distally located tissue.

24 Claims, 4 Drawing Sheets

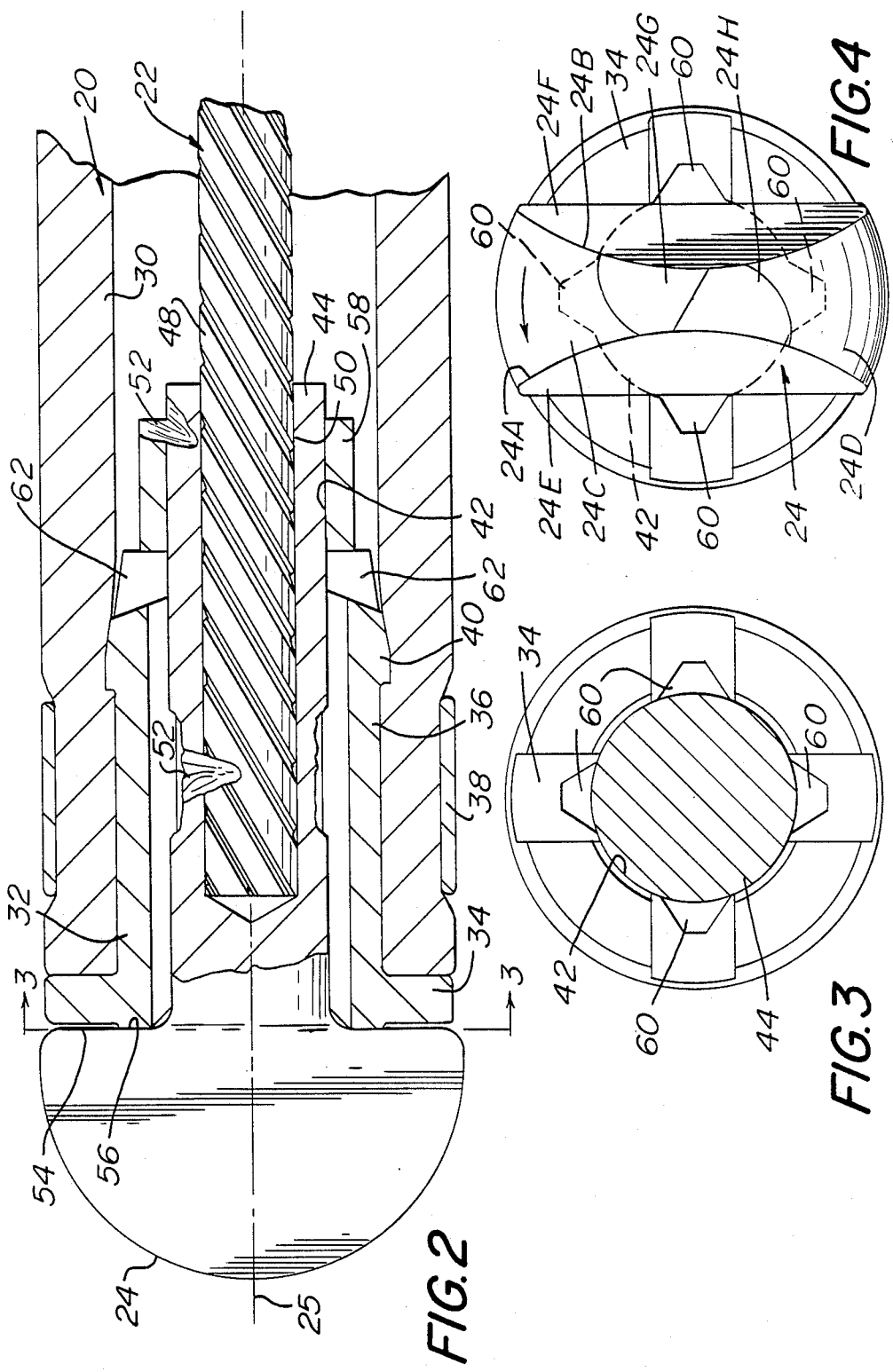

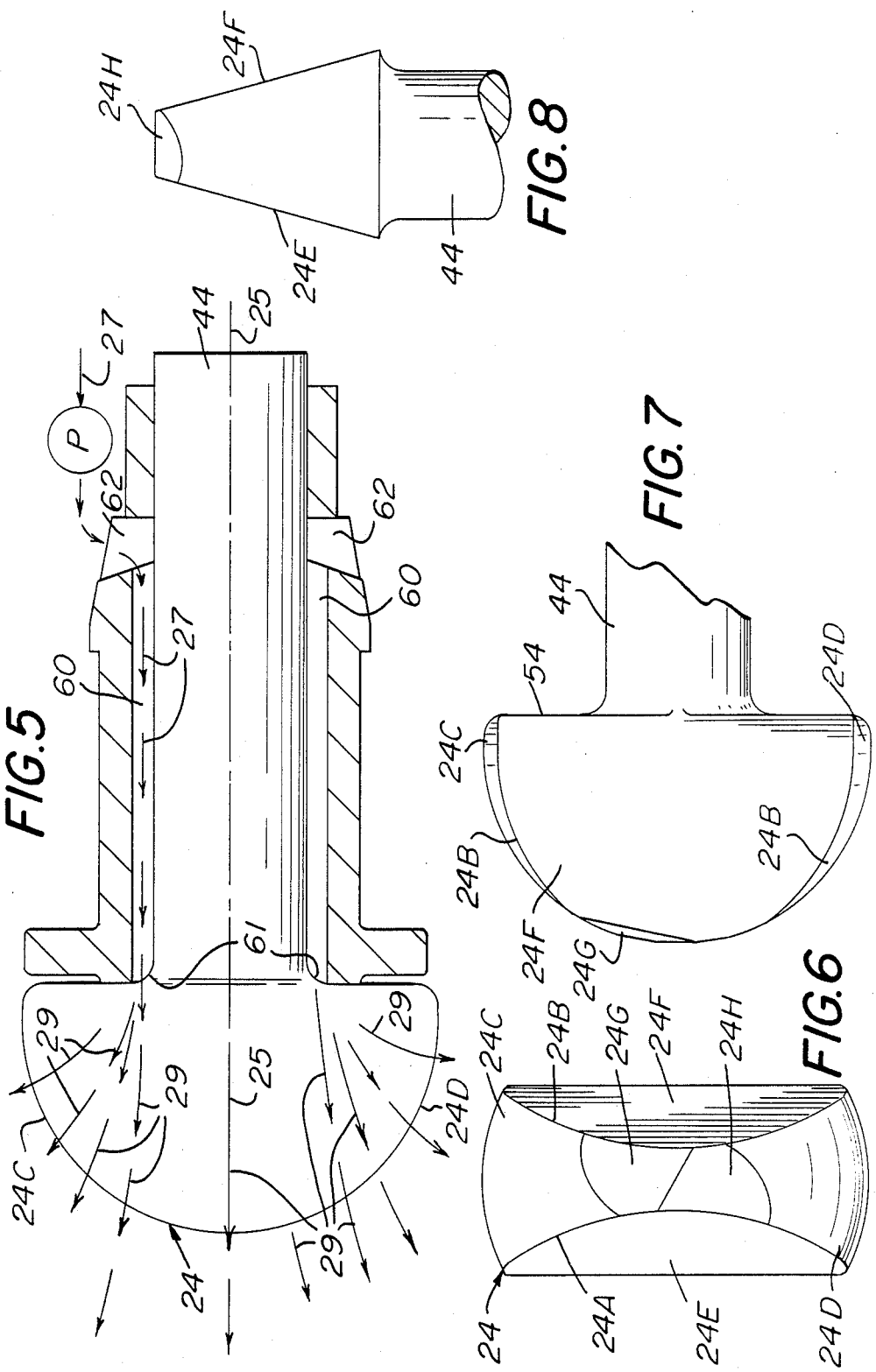

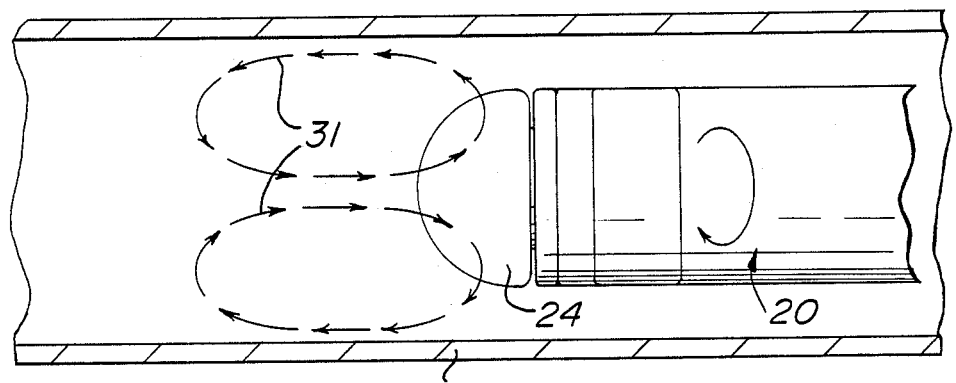
FIG. 9
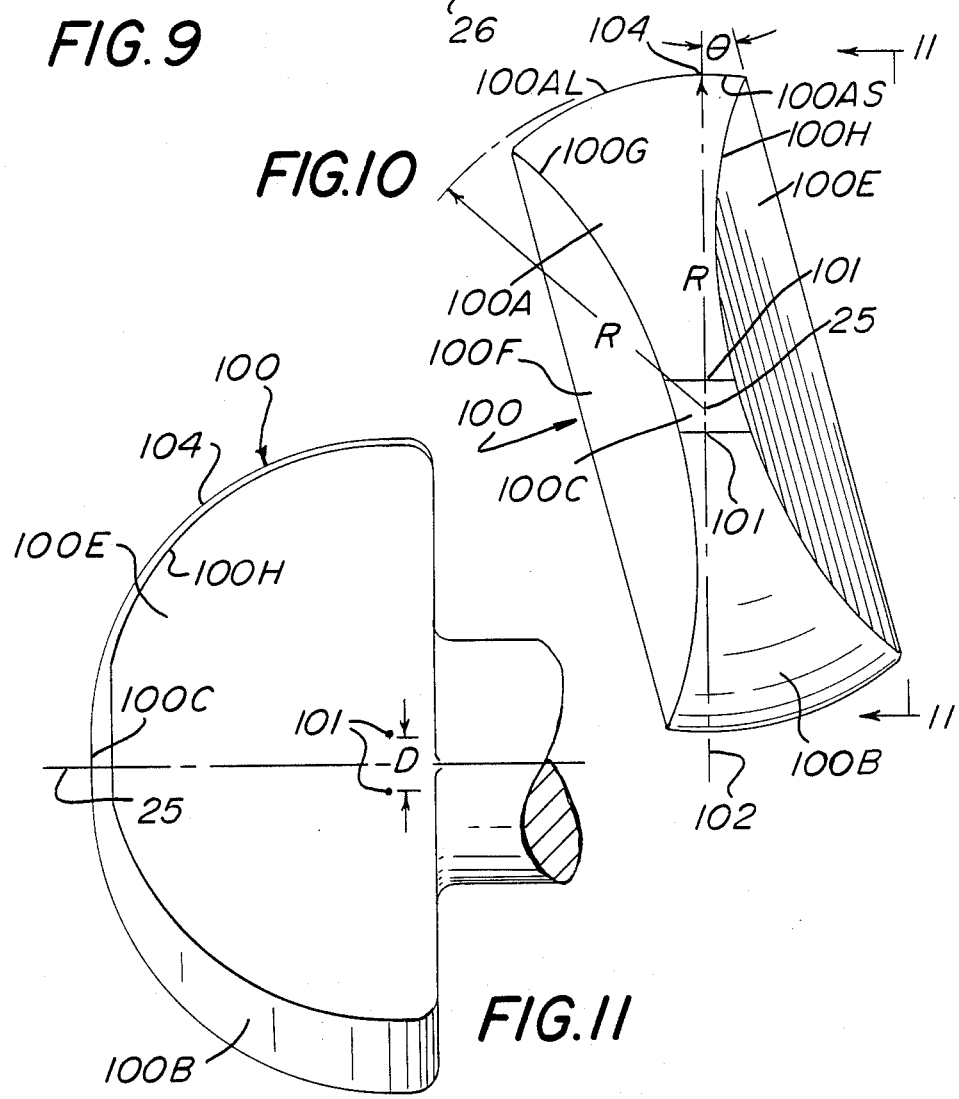
FIG. 10
FIG. 11

CATHETER WITH HIGH SPEED MOVING WORKING HEAD

BACKGROUND OF THE INVENTION

This invention relates generally to medical devices and more particularly to flexible, power-driven catheters for intravascular surgery and other surgical procedures.

Heretofore, the only interventional methods for treating atherosclerotic disease involves surgery for bypassing or remolding obstructive atherosclerotic material. Lasers have been suggested and are under investigation for transluminal revascularization. However, such devices have not been found common acceptance in medical practice because of various technical difficulties, the most serious of which being their tendency to perforate arterial tissue.

In U.S. Pat. No. 4,445,509 (Auth) there is disclosed a recanalization catheter designed specifically for cutting away hard, abnormal deposits, such as atherosclerotic plaque, from the inside of an artery, and while supposedly preserving the soft arterial tissue. That recanalization catheter includes a sharp edged, multi-fluted, rotary cutting tip mounted at the distal end of the catheter and arranged to be rotated by a flexible drive shaft extending down the center of the catheter. The rotation of the cutting head is stated as producing a "differential cutting" effect whereupon relatively hard deposits are cut away from relatively soft tissue. Suction ports are provided in the cutting tips to pull the hard particles produced by the cutting action into the catheter for removal at the proximal end thereof so that such particles do not flow distally of the catheter where they could have an adverse effect on the patient's body.

It has been determined that the use of sharp rotary cutting blades in a revascularization catheter can have various adverse effects on the arterial tissue, e.g., snagging, cutting or otherwise damaging the tissue of the artery wall.

OBJECTS OF THE INVENTION

Accordingly, it is the general object of the instant invention to provide catheters which overcome the disadvantages of the prior art.

It is a further object of the instant invention to provide a catheter having a working head which is arranged for high speed movement to effect a surgical or medical procedure within the body of a being and without significant damage to adjacent tissue.

It is a still further object of the instant invention to provide a catheter having a working head which is arranged for high speed movement to effect the opening of a restriction in a lumen and without damaging the lumen itself.

It is still a further object of the instant invention to provide a catheter for intralumenal use which effects the dilation of the lumen without damaging the tissue thereof.

It is still a further object of the instant invention to provide a catheter for use in opening restrictions formed of an undesirable material in a portion of a lumen by dilating the lumen and/or removing some of said undesirable material, allowing it to flow distally, all without resulting in injury to the patient.

SUMMARY OF THE INVENTION

These and other objects of the invention are achieved by providing a catheter for introduction into a lumen in a living being to open a restriction formed of an undesirable material in a portion of the lumen. The catheter comprises an elongated flexible member having a longitudinal axis, a working head located adjacent the distal end thereof and drive means therefor. The working head comprises at least one, non-sharp, impacting surface. The drive means is arranged for effecting the high speed movement of the working head to impact the undesirable material and thereby open said restriction.

DESCRIPTION OF THE DRAWING

Other objects and many of the attendant advantages of this invention will become readily appreciated when the same becomes better understood by reference to the following detailed description when considered in connection with the accompanying drawing wherein:

FIG. 2 is a side elevational view, partially in section, showing the distal end of the catheter shown in FIG. 1;

FIG. 3 is a sectional view taken along Line 3—3 of FIG. 2;

FIG. 4 is an end view of the catheter shown in FIG. 2;

FIG. 5 is a side elevational view of a portion of the distal end of the catheter of FIG. 1 and showing the expulsion of fluid therefrom during operation of the catheter;

FIG. 6 is a front elevational view of the working head or tip of the catheter shown in FIG. 1;

FIG. 7 is a side elevational view of the tip shown in FIG. 6;

FIG. 8 is another side elevational view of the tip shown in FIG. 6;

FIG. 9 is a side elevational view of a catheter like that shown in FIG. 1 located within a bodily lumen, e.g., artery, and illustrating the creation of vortex flow adjacent the working head during the operation of the catheter;

FIG. 10 is an enlarged front elevational view of an alternative working head or tip to that shown in FIG. 6; and FIG. 11 is an enlarged side elevational view of the alternative working tip shown in FIG. 10.

DETAILED DESCRIPTION OF THE PREFERRED EMBODIMENT

Figure 1:
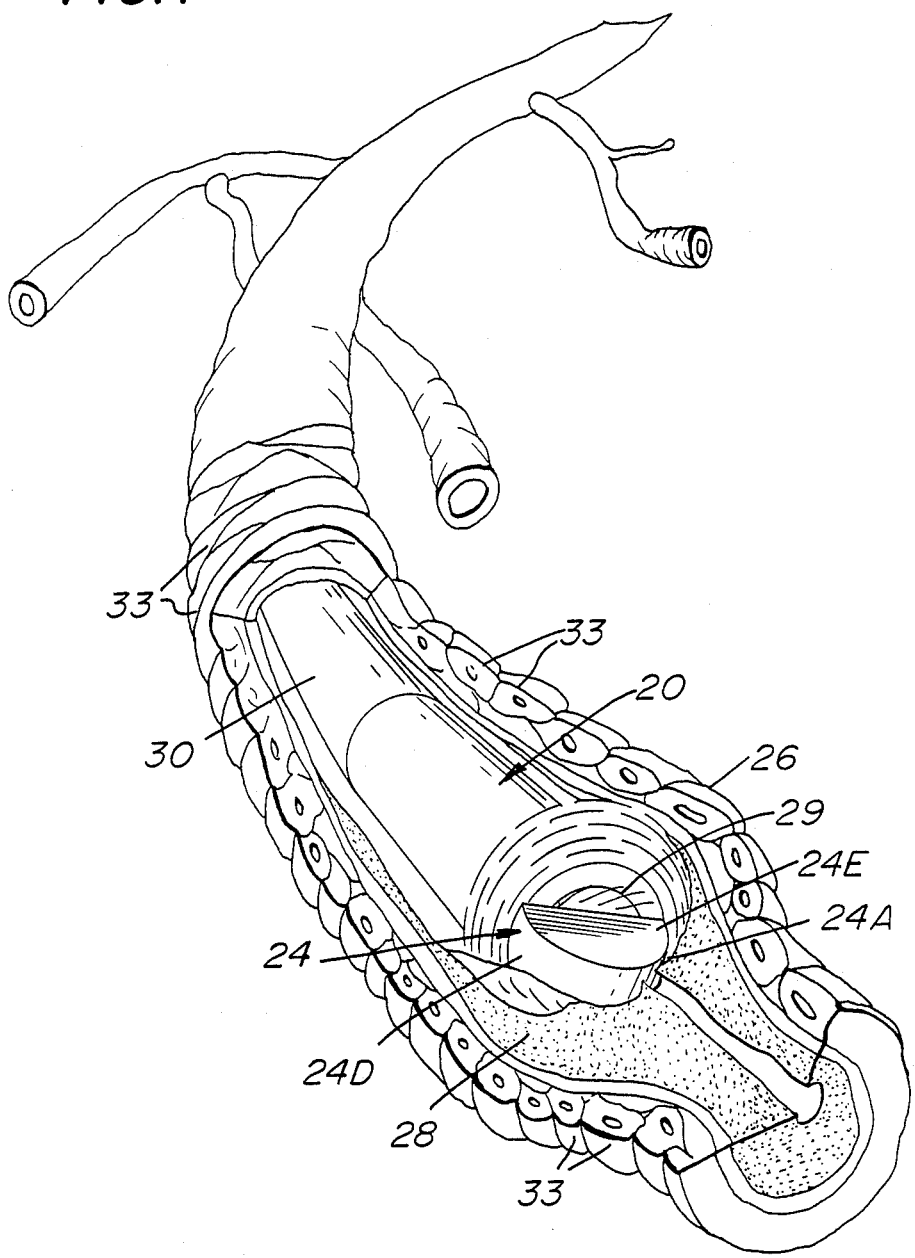
FIG. 1 is a perspective view, partially in section, showing the operation of the catheter of the subject invention in an artery restricted by occlusive atherosclerotic disease and illustrating the dilation and restriction opening properties of the catheter.

Referring now in greater detail to the various figures of the drawing wherein like reference characters refer to like parts, there is shown in FIG. 1 the distal end of a catheter 20 for intravascular or other surgical applications, e.g., fallopian tube dilation. The catheter 20 is an elongated member including a flexible drive assembly 22 (only a portion of which can be seen in FIG. 2) located therein. The drive assembly is preferably constructed in accordance with the teachings of our copending U.S patent application Ser. No. 746,220, filed on June 19, 1985, entitled Spiral Wire Bearing for Rotating Wire Drive Catheter, now U.S. Pat. No. 4,686,982 assigned to the same assignee as this application and whose disclosure is incorporated by reference herein. That drive assembly is particularly suited for in-body surgical applications, but can be used for other applications requiring the transmission of power at high speed and low torque, through a very narrow path, including bends of small, e.g., 0.75 inches (1.9 cm) radius of curvature. Located at the distal end portion of the catheter 20 is a working head or tool 24. The working head is arranged to be moved at a high speed with respect to the catheter by the drive means to effect the surgical procedure to be carried out by the catheter. The proximal end of the drive means of the catheter and which is located outside the patient's body is adapted to be connected to a source of rotary power, e.g., an electric motor (not shown). In the preferred embodiment disclosed herein, the drive means 22 effects the rotary movement of the working head 24 under the power provided from the remote power source (motor).

When the catheter 20 is used for treating occlusive atherosclerotic disease, such as opening a restriction in an artery formed by atherosclerotic plaque, the catheter 20 is introduced into the vascular system of the patient such as through an opening in the femoral artery at a point in the groin. The catheter is then guided through the vascular system of the patient to the site of the vascular occlusion or blockage that has been determined to exist so that its working head 24 is located immediately adjacent the restriction. In the illustration in FIG. 1, the working head 24 is shown in position in a coronary artery 26 immediately adjacent a restriction 28, e.g., partial occlusion or full occlusion which is to be opened to the freer flow of blood therethrough.

As will be recognized by those skilled in the art, such arterial restrictions are formed by the deposit of atherosclerotic plaque or some other material(s), such as wax and/or calcified athoroma, thickened and/or ulcerated intima, etc. Once in position, the catheter 20 is arranged to transluminally recatherize the diseased artery by dilating the stenotic or occluded area (which may or may not be covered by fibrous plaque) and/or selectively removing calcified thrombotic, or fatty tissue unprotected by fibrous plaque while alowing the artery wall to remain intact.

The details of the construction and operation of the catheter will be described later. Suffice now to state that the working head 24 includes a pair of non-sharp impacting surfaces 24A and 24B for impacting the material forming th restriction. The impacting surfaces 24A and 24B are formed by rounded or radiused edges of a respective pair of cam surfaces 24C and 24D. The cam surfaces are clearly shown in FIGS. 2, 4 and 6 and are formed by those convex outer surface portions of the working head located between a pair of relieved, e.g., flat, surfaces 24E and 24F. The working head 24 is arranged to be rotated about the longitudinal axis 25 (FIG. 2) of the catheter at a high rate of speed, e.g., from 10,000 rpm to 200,000 rpm. At the same time, fluid 27 (FIG. 5) is passed through the catheter and out of the base of the working head at the distal end of the catheter adjacent the central longitudinal axis thereof as shown in FIG. 5. The opening of the restriction to allow freer flow of blood is effected by the dilation and/or selective emulsification properties of the catheter's working head. In this connection, during the operation of the catheter 20 (to be described in considerable detail later), the fluid jets exiting the distal end of the catheter at the rotating working head are immediately accelerated laterally by the relieved, e.g., flatted, surfaces. The fluid stream is thus broken up into small segments, bullets or slugs 29 (FIG. 5) that develop considerable momentum as they are flung radially outward toward the wall of the artery. These liquid slugs transfer their momentum to the artery wall, helping to force the artery wall outward laterally in all directions, thereby dilating it. The liquid also serves as a lubricant for the working head-tissue interface, a coolant to maintain the tissue temperature within acceptable limits, and a carrier for radiopaque media and/or other medications. The rotating working head with its non-sharp impacting surfaces 24A and 24B also serves to differentiate atherosclerotic tissue from normal tissue through the inherent differences in the tissue's physical properties and organizational patterns. Therefore, when the catheter is passed transluminally through a diseased artery, the device's working head serves to emulsify occlusive lesions not covered with fibrous plaque by repeatedly impacting the material forming the restriction as the working head is rotated and with minimal risk of puncture or perforation of the contiguous arterial wall.

The non-sharp impacting surfaces 24A and 24B of the rapidly rotating working head removes atherosclerotic tissue by emulsification and differentiates the diseased tissue from the relatively undiseased tissue by using two properties found in normal tissue that is not found in most, if not all, atherosclerotic tissue. In this connection, when an artery wall is in contact with the high rotary speed working head, its most important protective property is its viscoelasticity. Simply stated, the artery wall tissue yields repeatedly under stress of the cam surfaces of rotating working head and returns to its original shape only after some delay, (i.e., the relieved surface following the cam surface pass the tissue so that the stress is removed, whereupon the tissue is enabled to recover as a function of viscoelastic memory). That stress is applied to the artery wall by the rounded edge of each cammed surface of the rotating working head with each revolution. As will be appreciated from the discussion to follow, the degree of deformation of the artery wall is affected by the height and profile of the cam surfaces and contiguous radiused impacting surfaces, and the axial load applied thereto by the operator. The degree of deformation and the frequency at which it takes place in turn define the energy the arterial tissue absorbs and, hence, the damage created. Damage to the artery wall can thus be reduced several ways, namely, keeping the height of the tissue engaging surfaces relatively small, making the cam profile a gentle rise, utilizing a high speed (frequency) revolution (tissue will essentially remain in its deformed state, touching only the outermost rounded edges of the working head adjacent each cam surface), and by keeping the axial load low to limit the stress on the artery wall. By appropriate selection of these parameters, the working head will do little or no damage to non-diseased tissue and will not puncture or otherwise perforate the artery wall except under excessive force or where the artery wall is totally diseased (e.g., non-viscoelastic as occurs in the case of a Monckeberg's sclerosis).

Fibrous plaque, unlike most diseased tissue, is viscoelastic and is undamaged when the rotating working head with its cam surfaces pass over it. The rounded edged cam surfaces have great difficulty in penetrating the fibrous plaque. Therefore, in a stenotic or occlusive lesion where fibrous plaque lines the obstructive lesion, dilation rather than selective emulsification plays the major role in reestablishing blood flow.

In contrast, atherosclerotic tissue is not viscoelastic. If calcific, fatty, thrombotic or a combination of all three exist and are not protected by fibrous plaque, such material will not yield under the stress induced by the rotating working head. Instead, such material absorbs the high frequency energy transmitted by the work head's impacting surfaces and the material is emulsified. The emulsification process is accomplished by the repeated impaction of the non-sharp impacting surfaces on the restriction forming material. Such action causes the material to be broken away in small particles. The catheter of the subject invention produces a powerful vortex flow illustrated diagrammatically and identified by the reference numeral 31 in FIG. 9. This vortex works in conjunction with the rotating working head so that the particles produced by the impacting action are repeatedly impacted over and over, so that upon each impaction their size is reduced further until the resulting particle size is sufficiently small that the particles can be permitted to flow downstream tissue without causing any significant deleterious effects to the patient. In this connection, it has been determined that in a typical operation 95% of the particles created during the impacting or emulsification process have a surface area smaller than that of a red blood cell.

A second important protective property inherent in nondiseased artery walls is its highly organized fibrous structure. Thus, as can be seen in FIG. 1, the fibers 33 of an artery wall 26 run circumferential to the lumen of the artery and generally perpendicular to the impacting surfaces 24A and 24B of the working head where they meet. This perpendicular line between those impacting surfaces and the arterial wall fibers is protective. Thus, the rotating working head does not separate the fibers. Instead, they remain organized in parallel, resisting separation and penetration. The energy absorbed from the rotating working head is distributed through the many fibers, thereby reducing the destructive force applied per fiber. Accordingly, individual fibers are undamaged and the artery wall remains intact.

Like most pathologic tissue, atherosclerotic tissue is distinctively different from non-diseased tissue in one major respect, lack of unified organization. Thus, when such tissue is engaged by the rotating working head, minute portions of the atherosclerotic tissue must absorb the impacting surfaces' energy alone. Accordingly, a particle of the material breaks off from the adjacent tissue. As mentioned earlier and as will be described in detail later, the operation of the rotary working head creates a vortex flow 31 adjacent the working head which causes the particles broken away by the action of the working head to be repeatedly impacted by the non-sharp, impacting surfaces 24A and 24B, thereby breaking those particles into smaller and smaller particles until they become part of what is effectively a highly emulsified solution.

The exact physiological reaction of the artery to the action of the working head is not known at this time. What is known is that the walls of the artery itself become dilated and remain dilated even after the catheter and its working head is withdrawn. In particular, it has been determined by angiogram and other testing procedures that after one has passed the working head of a catheter past the restriction that the walls of the artery have become stretched or dilated and remain such. More particularly, it has been found that the adventicia and media portions of the artery are stretched, while the intima (lining portion, which is most commonly the diseased portion) is fractured and fissured. Such action ensures that the restriction is thus "opened" to freer blood flow therethrough. Based on experience with balloon angioplasty the fracturing or fissuring of the intima enables renewed blood flow and naturally bodily processes to remodel and shrink the lesion in many cases.

Among the factors which may play a part in the restriction opening process is the changing or rearrangement of the vessel structure, e.g., vessel fibers, etc., due to any one or more of the following: Mechanical stretching of the lumen structure resulting from the size of the working head (a static effect) and/or the dynamic effect of cyclical high speed mechanical movement, e.g., rotation of the working head; increase in temperature of the lumen structure resulting from the mechanical cycling of the viscoelastic properties of the lumen tissue, bombardment with liquid propelled at the lumen wall by the rapid movement, e.g., rotation, of the working head, whereupon the head pressure of the liquid impacting the walls exceeds the normal local blood pressure; forcing or wedging of liquid into the lumen walls by mechanically induced film pressure as the working head's cammed and impacting surfaces slide over the lumen surface, whereupon the tissue fibers are forced apart; and forcing of liquid into the lumen walls by the local dynamic or hydrostatic pressure induced by the injected liquid and/or the moving working head. Other, as yet undetermined, factors may also play a part in the dilation process.

Referring to FIG. 2, the details of the distal end of a preferred embodiment of the catheter 20 will now be described. As can be seen the catheter 20 basically comprises an elongated, flexible tubular member or jacket 30 which is formed of a suitable material, e.g., plastic, and which has a small outside diameter. In a preferred embodiment shown herein the outside diameter is approximately 1.7 mm (5 French) or less. This size catheter is merely exemplary. Thus, in accordance with this invention, the catheter can be constructed as small as 2 French (0.67 mm).

At the distal end of the catheter 20 there is secured a sleeve-like bushing 32. The bushing includes a flanged end face 34 arranged to abut the end of the catheter's jacket 30 and a tubular portion 36. The outside diameter of portion 36 is approximately that of the inside diameter of the catheter's jacket 30 so that it is snugly fit therein. The bushing is held firmly in place by a retaining band 38 which tightly encircles the periphery of the catheter jacket 30 so that plural gripping teeth 40 located about the periphery of the tubular portion 36 dig into the interior surface of the catheter jacket 30 and hold the bushing tightly in place therein. The bushing 32 also includes a through bore 42 (FIGS. 2 and 3) extending theretnrough and aligned with the longitudinal central a is 25 of the catheter. The working head 24 includes a mounting shank or axle 44 projecting proximally and passing through the bore 42 in the bushing 32. A multistrand drive cable 48 constructed in accordance with the teachings of our aforementioned copending U.S. patent application Ser. No. 746,220 extends down the catheter's jacket 30 coaxial with axis 25 and terminates and is disposed within a longitudinal extending bore 50 in the shank 44 of the working head 24. The end of the drive cable 48 is secured in place in the bore 50 via a laser weld joint 52. The shape of the working head 24 will be described later. Suffice now to state that it includes a generally planar rear surface 54 which engages the front surface 56 of the bushing flange 34. The working head 24 is prevented from axial movement within the bushing 32 by virtue of a retaining ring 58 mounted on the proximal end of the working head axle 44 contiguous with the proximal end of the bushing. The retaining ring 58 is secured to the proximal end of the working head axle 44 via another laser weld 52.

The drive cable 48 is supported in the central position along axis 25 by means of a spiral bearing (not shown) also constructed in accordance with the teachings of our aforenoted copending patent application Ser. No. 746,220. That bearing member thus comprises a helical or spiral cylindrical coil of wire surrounding the multi-strand drive cable 48. The spiral bearing extends substantially the entire length of the catheter from a proximately located point adjacent the drive motor (not shown) to the distal end of the catheter. The outer diameter of the helical bearing coil is sufficiently great so that its loops just clear the interior surface of the catheter's jacket 30 to hold the bearing securely in place therein. The inside diameter of the central passageway extending down the length of the helical bearing is just slightly greater than the outside diameter of the drive cable 48 so that the drive cable can freely rotate therein.

It should be pointed out at this juncture that the drive cable 48 can, if desired, be drawn or swaged so that its outer periphery of the cable has a greater contact surface area with the spiral bearing than if the cable were unswaged. This feature is shown and claimed in our copending U.S. patent application Ser. No. 938,698, filed on Dec. 5, 1986, and entitled Catheter With Means To Prevent Wear Debris From Exiting. Also disclosed and claimed in that application is a spiral bearing wire whose inner surface, that is, the surface defining the central passageway therethrough, is substantially planar in order to further increase the engaging surface areas. A bearing constructed in accordance with that feature can, if desired, be used to support the drive cable 48 herein.

With such a construction, the drive cable 48 can be rotated at a high rate of speed, e.g., from 10,000 to 200,000 rpm, while the catheter is bent through a small radius of curvature, e.g., 0.75 inches (1.9 cm), and without the creation of any standing waves which could result in unwanted vibration to the catheter.

The spacing between the convolution of the spiral bearing, the inner surface of the catheter tube 30 and the outer surface of the drive cable 48 form a passageway (not shown) throuqh which a fluid (liquid) can flow from the proximal end of the catheter to the distal end. This liquid can be utilized to cool or lubricate the bearing system. Moreover, as will be described in detail later, and as mentioned earlier, this liquid is expelled at the rotating working head to aid in the dilation of the arterial tissue at the working head. Moreover, the liquid which is passed down the catheter can, if desired, be oxygenated to eliminate distal ischemia during the restriction opening procedure by the catheter. Also, if desired, nitrates, contrast media or other drugs can be added to the liquid as needed during the procedure.

The means for enabling the liquid to exit the catheter at the distal end will now be described with reference to FIGS. 2, 4 and 5.

Thus, as can be seen therein, extending down the central bore 42 of the bearing 32 are four, equidistantly spaced, grooves 60. The distal end of each groove 60 terminates at a fluid exit port 61 located at the distal end flange 34 of the bushing, while the proximal end of each groove 60 terminates in a respective, generally radially extending, relief groove 62. The fluid (liquid) 27 passing down the interior of catheter tube 30 flows under pressure (denoted by the character P in FIG. 5) into the relief grooves 62, through the associated longitudinal grooves 60 and out through the ports 61 at the end face of the catheter closely adjacent to the longitudinal axis 25.

The details of the working head 24 will now be discussed. As can be seen in FIGS. 2, 4, 6, 7 and 8, the working head 24 basically comprises a convex shaped tip of a generally hemispherical shape and having a pair of generally planar diametrically disposed side faces heretofore referred to as relieved surfaces 24E and 24F. Thus, the cam surfaces formed therebetween are sections of the surface of a sphere. The interface of the cam surfaces 24C and 24D with the relieved surfaces 24E and 24F are rounded (radiussed) so that each interface surface is not sharp (although in the scale of the drawings herein it may appear to be a sharp line). As can be seen in FIG. 8, the relieved surfaces 24E and 24F taper toward each other in the direction toward the distal end of the working head, with the maximum spacing between the relieved surfaces being approximately the diameter of the working head shaft 44. Thus, the flatted or relieved surfaces are at a negative rake angle to the cam surfaces. Further details of the working head will be described later.

As can be seen in FIG. 4, by virtue of the shape of the working head as described above the fluid exit ports 61 at the distal end of two diametrically disposed grooves 40 are uncovered or exposed by the relieved surfaces 24E and 24F to enable fluid 27 passing through those grooves to exit the ports 61. As will be appreciated by those skilled in the art, since the working head rotates, the relieved surfaces of the working head sequentially cover and uncover diametrically opposed ports 61 at the distal ends of the grooves. This action breaks up the fluid streams 27 exiting from those ports into the previously mentioned segments or slugs 29.

The fluid velocity is determined by the pressure at the point P in FIG. 5. For catheters of an 8 F (French) size, and whose working head is of 0.05 inches radius a pressure of approximately 30 pounds per square inch is deemed sufficient to ensure that some liquid streams flow axially along axis 25 so that the exiting liquid is distributed in a generally hemispherical pattern about the working head. For catheters of 5 F (French), a pressure of 100 PSI is sufficient. Accordingly, with sufficent fluid pressure applied some of the liquid streams reach the end of the tip contiguous with the longitudinal central axis 25 while other streams are cut off and accelerated at an acute angle thereto and still further streams are cut off and accelerated almost radially. Accordingly, with a working head and catheter constructed as described, the fluid exiting from the ports is distributed almost hemispherically around the tip without the need for a central hole therein.

In order to prevent heat induced injury to the artery, sufficient luquid should be expelled into the restriction at the working head. It has been found that 30 ccs per minute is suitable for an 8 F (French) instrument while 20 ccs per minute is suitable for a 5 F instrument.

As will be appreciated by those skilled in the art, many of the liquid slugs 29 have some radial component and develop tremendous momentum as they are flung outwards toward the artery wall. The momentum of the slugs is transferred to the artery wall, thereby forcing the wall laterally outward in all radial directions to dilate it, as described earlier.

Tests have shown that the radial pressure developed by the rotating working head is substantial and can raise local static pressure immediately adjacent the working head by approximately 100 to 200 millimeters of Hg. This increased pressure on the artery wall contiguous with the rotating working head is not due solely to the impact of the fluid slugs thereon, but is also due to the recirculation of the fluid surrounding the working head. In this connection, as noted earlier, the rotation of the working head about axis 25 produces a powerful, toroidal shaped vortex 31 contiguous with the working head as shown in FIG. 9. The vortex 31 in addition to augmenting the application of increased pressure to the artery wall contiguous with the working head, also has the effect of recirculating any particles that may have been broken off from the restriction by the impact of the rotating working head with the material forming the restriction. Thus, if the material forming the restriction is such that particles are broken away they are circulated by the vortex and carried back into the rotating working head where they are progressively reduced in size. This progressive size reduction action has the result of producing particles which, as noted earlier, are safe to flow distally.

The impacting surfaces 24A and 24B, i.e., the interfacial areas at which the spherical section cam surfaces 24C and 24D meet the relieved surfaces 24E and 24F, are of sufficiently large radius to ensure that no damage to the healthy tissue of the artery occurs when those surfaces impact arterial tissue. In this regard, the viscoelastic nature of healthy tissue as well as diseased soft tissue is such that such soft materials can be stretched and negotiated by the rotating working head if its impacting surfaces are of sufficiently large radius that they allow the arterial tissue (in the form of a wave of tissue) to flow smoothly thereunder. At typical operating speeds the viscoelastic tissue wave is on the order of several thousands of an inch high. As long as the radius of the impacting surfaces 24A and 24B is of the order or greater than the tissue wave height, the tissue will not rupture during stretching. It has been found that for a working head like that shown herein and having two cam surfaces and running between 10,000 and 100,000 rpm a radius of 0.0015 for the impacting surfaces 24A and 24B is sufficient, providing the surgeon using the instrument is relatively skilled. A working head having an impacting surface whose radius is from 0.002 to 0.003 would be better to ensure that no damage results from the catheter's use by less skilled surgeons. Moreover the cam surface passing frequency, that is, the velocity of the cam surface coupled with the length of the cam surface should be large enough that the tissue cannot recover substantially before the next impacting surface arrives. This allows quite aggressive instrument feed rates without puncture. In this connection, it is suggested that the velocity of the impacting surfaces 24A and 24B at their maximum distance from axis 25 be in the range from 100 to 2,000 centimeters per second. This speed range ensures that at the low end the impacting surfaces of the rotating working head always describe a fine helix in the artery even at high feed rates of the order of ten centimeters per second. This makes use of the protective nature of the tip travel along the axis of the circumferential arterial wall fibers. The radius of the impacting surfaces 24A and 24B should also not be too large. In this connection, as noted earlier, the rotating working head creates a powerful vortex for carrying any particles broken off from the material forming the restriction to be multiply impacted and subsequently reduced in size. Thus, in order not to compromise this action, it is necessary that the working head impacting surface radius not be too large to compromise such particle reduction action. For tips having an impacting surface radius of 0.002–0.003 inches the progressive particle reduction action operates at tip rotational speeds of 30,000 to 90,000 rpm.

As just discussed, injury to soft tissue is controlled by the impacting surface radius and its passing velocity and to a lesser degree by its and the contiguous cam surface's clearance. However, hard tissue seems to be dramatically affected by clearance, with the smaller clearance, the less chance of injuring or perforating the arterial tissue. Directional protection control can also be achieved by varying the clearance of the working head's impacting surface radius. Hence, as can be seen in FIGS. 6, 7 and 8, the portion of the working tip cam surfaces 24C and 24D contiguous with the rotational 25 is 45 is relieved by the formation of two diametrically opposed planar sections 24G and 24H. Thus, the radiussed impacting surfaces at the interface of the cam surfaces and the planar relieved surfaces have approximately zero degree clearance while the radiussed impacting surfaces at the interface of cam surfaces and the relieved surfaces form a ten degree clearance. Accordingly, the working head 24 of the subject invention has zero clearance at large radial distances from the rotational axis 25 and ten degree clearance at small radial distances. This feature compensates for the lower velocity of the impacting surfaces at smaller radial distances. Accordingly, in accordance with the subject invention, working heads can be produced to provide very small clearance at portions of the working head moving at high speed with respect to the material to be removed while providing some larger clearance at portions of the tip moving at lower speeds with respect to that material.

In order to produce an even more gentle action on the arterial tissue wave created by the rotating cammed working head, it can be constructed a shown in FIGS. 10 and 11 and denoted by the reference numeral 100. Thus, in the working head 100 embodiment shown in FIGS. 10 and 11, the convex cam surface is not of a constant radius of curvature. In this connection, as can be seen in FIGS. 10 and 11, the working head 100 includes two quadraspherical section cam surfaces 100A and 100B, each of which has the same radius of curvature. The centers of generation of the quadraspheres are denoted by the reference numeral 101 and are spaced (offset) from each other by a distance D (FIG. 11). Accordingly, the surfaces 100A and 100B are separated from each other by an intermediate surface 100C whose width is D. As can be seen in FIG. 11, the surface 100C is tangential to the ends of the opposed quadraspherical surfaces 100A and 100B and is linear between the ends of those surfaces when viewed in the direction of lines 11—11 in FIG. 10 but circular and of the same radius as surfaces 100A and 100B measured around an axis 102 (FIG. 10). The plane in which the axes 25 and 102 lie includes the two centers of generation 101 and bisects the working head 100 into two halves. That plane will be hereinafter referred to as the working head bisecting plane. In the embodiment 100 shown herein, the flatted or relieved surfaces 100D and 100E are similar to relieved surfaces 24E and 24F of working head 24. However, as can be seen in FIG. 10, the relieved surfaces 100D and 100E are oriented at an angle Θ with respect to the working head bisecting plane. Thus, the working head 100 is bisected into two symmetric portions by the working head bisecting plane. This construction results in the creation of a long ramp cam surface 100AL between the leading radiused impacting surface 100G and the highest point 104. The ramp can be appreciated by viewing the difference between the path of maximum radius R generated by the rotation of head 24 and the surface 100AL while creating a short ramp surface 100AS between point 104 and the trailing radiused impacting surface 100H. By virtue of the relatively long ramp cam surface 100AL leading to the point of maximum cam surface radius a gentle cam action results when the surface 100AL makes contact with the material forming the restriction to result in lower acceleration (less aggression) applied to the particles produced by that impact. In alternative embodiments of the working head 100 the head bisecting plane can be oriented so that the angle Θ is between zero degrees and any maximum angle. If the head bisecting plane is parallel to the relieved surfaces 100E and 100F so that the angle Θ is zero degrees then the leading and trailing cam surfaces 100AL and 100AS will be the sam length.

As should thus be appreciated by adjusting the orientation of the head bisecting angle, and hence the orientation of cam surfaces one can adjust the degree of aggression of the working head to a desired extent.

It should be pointed out at this juncture other shaped working heads in lieu of those disclosed herein can be constructed in accordance with this invention. Thus, the cam surfaces need not be portions of a spherical surface, but can be ovoidal, conical or any other suitable shape. Moreover, the relieved surfaces need not be planar, but can be arcuate, multiplanar (portions in different planes), etc. Furtherstill, the impacting surfaces need not be of a constant radius so long as they are sufficiently rounded or arcuate to be substantially equal to or larger than the tissue wave to be created by the rotation of the working head.

The vortex created by the rotation of the working head is effective in stopping large particles from passing downstream (distally). In this regard, it provides a very effective and important mechanism against macroembolization and distal infarction. Any particle that may break off distally or proximally to the rotating working head is immediately pulled into the vortex and its potential threat to a distal organ is terminated by its being reduced in size (repeatedly impacted to the point of emulsification).

The mechanical and fluid forces applied by the working head allow the catheter to track the point of least resistance in total occlusions. In this regard, the working head finds the area of least resistance by dissecting the tissue with fluid pressure as it moves forward. From observation, the point of least resistance is always in the lumen of the previously patent artery. It is therefore relatively easy and safe to open totally obstructed tortuous arteries with the subject catheter. In this connection, the working head finds the area of least resistance and serves to guide the catheter and not vice versa.

As will be appreciated by those skilled in the art, the catheter with its working head as disclosed and claimed herein has many properties useful in treating occulsive atherosclerotic disease. Moreover, the techniques for using the subject invention are simple and can be mastered easily and are moreover widely applicable to many organ systems relatively inexpensively and should be associated with low morbidity.

It should also be appreciated by those skilled in the art, that the catheter of the subject invention as well as its method of use enable coronary as well as peripheral, e.g., leg, revascularization of patients either intraoperatively or percutaneously, thereby providing methods of treatment which are less invasive, less expensive and less time consuming than prior art techniques. Moreover, the catheters of the subject invention enable revascularization of smaller arteries and longer lesions than otherwise possible. Thus, with the subject invention one can prophylactically treat coronary artery disease, perhaps one of the most widespread diseases affecting Americans. It will also be appreciated by those skilled in the art that the subject catheters can be readily utilized to remove a thrombosis in a manner similar to the restriction opening process.

The subject catheters are also of significant utility for effecting tube or duct, such as eustachian tube, fallopian tube, etc., dilation. With regard to the latter, a substantial number of women in the United States are infertile due to fallopian tube malfunction or stricture. At present, there is no device or simple procedure to dilate or open the fallopian tube. In this connection, while microsurgical procedures to attempt to alleviate the occlusion or stenosis, the results nave been poor, the technique difficult and expensive and of limited availability. By utilizing the catheters of this invention one can pass such catheters via the cervical os to the fallopian tube to effect the dilation of the stenosis or occlusion in the same manner as described with reference to revascularization of arteries.

It has also been found that a catheter like those of this application can be utilized to stop spasm, i.e., uncontrolled constriction, in an artery or other lumen and for preventing it from going back into spasm. To that end, the catheter is inserted into the artery in spasm and operated, as described heretofore, whereupon the spasm immediately ceases and remains stopped even after the catheter is removed. While this effect, that is the stoppage and prevention of spasm, results from the use of catheters of this invention, the exact mechanism and exact physiological reaction of the lumen to the action of the catheter is unknown at this time. For example, the operation of the working head may cause the same effects discussed with respect to lumen dilation to occur to stop and prevent spasm. More particularly, the action of the working head may cause permanent change, e.g., damage to the neuromuscular junctions or muscles surrounding the lumen to prevent it from contracting. This antispasm technique is not limited to arterial or vascular applications. Hence, the technique can be used in any application where spasm of a tubular body is a problem, e.g., bronchial tubes, the bowl, the esophagus, etc. To that end, the subject catheters can be used with any tubular structure which may go into spasm. Moreover, the diameter of the tubular structure in spasm can be substantially larger, e.g., more than double the diameter, of the catheter with the antispasm procedure still being effective.

As should now be appreciated the subject invention provides a catheter for use in a wide variety of non (or minimum) invasive surgical procedures. Those procedures specifically mentioned and discussed herein are by no means the only such procedures. Thus, other surgical procedures requiring access to an operative point or situs from a remote location may also be accomplished using the catheters of the subject invention, with such access being achieved either intraoperatively, percutaneously, or via a natural orifice.

Without further elaboration, the foregoing will so fully illustrate our invention that others may, by applying current or future knowledge, readily adopt the same for use under various conditions of service.

We claim:

1. A catheter for introduction into a lumen in a living being to open a restriction formed of an undesirable material in a remote portion of said lumen, said catheter comprising an elongated member having a longitudinal axis, a working head located adjacent the distal end thereof, and drive means for effecting the rotation of said working head about said axis, said working head comprising at least one, non-sharp, arcuate impacting surface repeatedly impacting said material as said working head is rotated about said axis and producing a wave in the tissue of said lumen adjacent said impacting surface, said impacting surface defining at least one curve in a plane perpendicular to said axis, with the radius of curvature of said curve in said plane being substantially equal or greater than said tissue wave, whereupon the repeated impaction of said impacting surface on said undesirable material opens said restriction and reduces in size any portion of said undesirable material broken away by the impacting action of said impacting surface to enable said portion to flow distally without significant deleterious effects to distally located tissue.

2. The catheter of claim 1 wherein said restriction is opened by the dilation of said lumen portion adjacent said restriction resulting from said working head movement and/or the removal of some of said undesirable material resulting from said impacting surface impacting said undesirable material to break off portions therefrom to form particles, said particles being sufficiently small that they are enabled to flow distally without significant delterious effects to distally located tissue.

3. The catheter of claim 2 wherein said catheter includes means for producing a fluid flow adjacent said working head to carry said particles into repeated engagement with said impacting surface to successively reduce the size of said particles.

4. The cather of claim 3 wherein said working head is arranged for high speed rotation about said longitudinal axis.

5. The catheter of claim 4 wherein said fluid flow is a vortex flow produced by the rotation of said working head.

6. The catheter of claim 1 wherein said radius is in the range of 0.001 inch to 0.005 inch.

7. The catheter of claim 1 wherein said working head is arranged for high speed rotation about said longitudinal axis and wherein said non-sharp, impacting surface is formed by an arcuate surface adjacent at least one cam surface.

8. The catheter of claim 7 wherein a non-sharp impacting surfact is formed at the interface of said cam surface and a relieved surface.

9. The catheter of claim 7 wherein said cam surface is a portion of spherical surface and wherein said relieved surface is planar.

10. The catheter of claim 9 wherein said planar surface is skewed with respect to said lonqitudinal axis.

11. The catheter of claim 10 wherein said working head comprises a pair of cammed surfaces, and a pair of relieved, planar surfaces each of said planar surfaces being skewed with respect to said longitudinal axis, with said planar surfaces tapering toward each other in the direction of the distal end of said working head.

12. The catheter of claim 9 wherein said cam surfaces comprise a pair of substantially quarterspherical surfaces, said substantially quarterspherical surfaces being offset from each other by a tangential intermediate surface.

13. The catheter of claim 12 wherein said planar surface is skewed with respect to said longitudinal axis.

14. The catheter of claim 13 wherein said working head comprises a pair of cammed surfaces, and a pair of planar, relieved surfaces, each of said relieved surfaces being skewed with respect to said longitudinal axis, with said relieved surfaces tapering toward each other in the direction of the distal end of said working head.

15. The catheter of claim 14 wherein a plane bisecting the working head through said longitudinal axis extends at an angle to a plane of at least one of said relieved surfaces.

16. The catheter of claim 7 wherein said working head additionally comprises at least one relieved surface and said catheter additionally comprises means for ejecting a fluid at said working head, whereupon said relieved surface causes at least a portion of said fluid to be thrown in a direction having a component oriented outward radially with respect to said longitudinal axis.

17. The catheter of claim 16 wherein said means for ejecting a fluid comprises a fluid passageway having a port located adjacent said longitudinal axis, said port being arranged to be consecutively covered and uncovered by the rotation of said working head.

18. The catheter of claim 17 wherein said restriction is opened by the dilation of said lumen portion adjacent said restriction resulting from said working head rotation and/or the removal of some of said undesirable material resulting from said impacting surface impacting said undesirable material to break off particles therefrom, said particles being sufficiently small that they are able to flow distally without significant delterious effects to distally located tissue.

19. The catheter of claim 18 wherein the rotation of said working head produces a fluid flow adjacent said working head to carry said particles into repeated engagement with said impacting surface to successively reduce the size of said particles.

20. The catheter of claim 19 wherein said fluid flow is a vortex.

21. The catheter of claim 1 wherein said radius is in the range of 0.001 inch to 0.005 inch.

22. A method for opening a restriction formed of an undesirable material in a portion of a lumen in a living being using an instrument in said lumen at a location remote from said restriction, said instrument comprising a member having a longitudinal axis, a working head located at the distal end thereof, and drive means for effecting the rotation of said working head about said axis, said working head comprising at least one, non-sharp, arcuate impacting surface, said method comprising the steps of locating said working head in said lumen at the situs of said undesirable material, and operating said drive means to cause said working head to rotate, whereupon said impacting surface releatedly impacts said material and produces a wave in the tissue of said lumen adjacent said impacting surface, said impacting surface defining at least one curve in a plane perpendicular to said axis, with the radius of curvature of said curve in said plane being substantially equal or greater than said tissue wave so that the impaction of said impacting surface on said undesirable material thereby opens said restriction and reduces in size any portion of said undesirable material broken away by the impaction action of said impacting surface to enable said portion to flow distally without significant delterious effects to distally located tissue.

23. The method of claim 22 additionally comprising the steps of introducing a fluid into said lumen adjacent said working head and causing at least a portion of said fluid to flow outward, with some directional components of said flow being substantially outwardly radially, whereupon said restriction is opened by the dilation of said lumen portion adjacent said restriction resulting from said working head movement and/or the removal of some of said undesirable material resulting from said impacting surface impacting said undesirable material to break off portions therefrom to form particles, said particles being sufficiently small that they enabled to flow distally without significant delterious effects to distally located tissue.

24. The catheter of claim 23 wherein said working head is rotated at a high rate of speed and wherein said fluid flow adjacent said working carries said particles into repeated engagement with said impacting surface to successively reduce the size of said particles.

* * * * *